US011036758B2

(12) United States Patent
Dageville et al.

(10) Patent No.: US 11,036,758 B2
(45) Date of Patent: *Jun. 15, 2021

(54) ADAPTIVE DISTRIBUTION METHOD FOR HASH OPERATIONS

(71) Applicant: SNOWFLAKE INC., San Mateo, CA (US)

(72) Inventors: Benoit Dageville, Seattle, WA (US); Thierry Cruanes, San Mateo, CA (US); Marcin Zukowski, San Mateo, CA (US); Allison Waingold Lee, San Carlos, CA (US); Philipp Thomas Unterbrunner, Belmont, CA (US)

(73) Assignee: Snowflake Inc., San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/085,987

(22) Filed: Oct. 30, 2020

(65) Prior Publication Data
US 2021/0049187 A1  Feb. 18, 2021

Related U.S. Application Data

(63) Continuation of application No. 16/858,510, filed on Apr. 24, 2020, now Pat. No. 10,838,978, which is a
(Continued)

(51) Int. Cl.
*G06F 16/27* (2019.01)
*G06F 9/50* (2006.01)
*G06F 16/14* (2019.01)
*G06F 16/21* (2019.01)
*G06F 16/22* (2019.01)
(Continued)

(52) U.S. Cl.
CPC ............ *G06F 16/27* (2019.01); *G06F 9/4881* (2013.01); *G06F 9/5016* (2013.01); *G06F 9/5044* (2013.01); *G06F 9/5083* (2013.01); *G06F 9/5088* (2013.01); *G06F 16/148* (2019.01); *G06F 16/1827* (2019.01); *G06F 16/211* (2019.01); *G06F 16/221* (2019.01); *G06F 16/2365* (2019.01); *G06F 16/2456* (2019.01); *G06F 16/2471* (2019.01); *G06F 16/24532* (2019.01); *G06F 16/24545* (2019.01); *G06F 16/24552* (2019.01); *G06F 16/951* (2019.01); *G06F 16/9535* (2019.01);
(Continued)

(58) Field of Classification Search
CPC ............ H04L 67/2842; H04L 67/1097; H04L 67/1095; G06F 9/5088; G06F 9/5083; G06F 9/5044; G06F 9/5016; G06F 9/4881; G06F 16/951; G06F 16/24532; G06F 16/2365; G06F 16/9535; G06F 16/2456; G06F 16/211; G06F 16/1827; G06F 16/148; G06F 16/24552; G06F 16/221; G06F 16/2471; G06F 16/27
USPC ........................................ 707/714
See application file for complete search history.

(56) References Cited

U.S. PATENT DOCUMENTS 4,967,341 A * 10/1990 Yamamoto ........ G06F 16/24561
5,812,840 A *  9/1998 Shwartz .............. G06F 16/2423
(Continued)

*Primary Examiner* — Hanh B Thai
(74) *Attorney, Agent, or Firm* — Womble Bond Dickinson (US) LLP

(57) ABSTRACT

A method, apparatus, and system for join operations of a plurality of relations that are distributed over a plurality of storage locations over a network of computing components.

30 Claims, 11 Drawing Sheets

Related U.S. Application Data continuation of application No. 16/039,710, filed on Jul. 19, 2018, now Pat. No. 10,997,201, which is a continuation of application No. 14/626,836, filed on Feb. 19, 2015, now Pat. No. 10,055,472.

(60) Provisional application No. 61/941,986, filed on Feb. 19, 2014.

(51) Int. Cl.

| | | |
|---|---|---|
| *G06F 16/951* | (2019.01) | |
| *G06F 16/182* | (2019.01) | |
| *G06F 16/23* | (2019.01) | |
| *G06F 16/2455* | (2019.01) | |
| *G06F 16/2458* | (2019.01) | |
| *G06F 16/9535* | (2019.01) | |
| *G06F 16/2453* | (2019.01) | |
| *G06F 9/48* | (2006.01) | |
| *H04L 29/08* | (2006.01) | |

(52) U.S. Cl.
CPC ...... *H04L 67/1095* (2013.01); *H04L 67/1097* (2013.01); *H04L 67/2842* (2013.01)

(56) References Cited

U.S. PATENT DOCUMENTS

| | | | |
|---|---|---|---|
| 5,873,074 A | 2/1999 | Kashyap et al. | |
| 6,112,198 A | 8/2000 | Lohman et al. | |
| 6,185,557 B1 | 2/2001 | Liu | |
| 6,374,235 B1 | 4/2002 | Chen et al. | |
| 6,865,567 B1 | 3/2005 | Oommen et al. | |
| 7,092,951 B1 | 8/2006 | Luo et al. | |
| 7,092,954 B1 | 8/2006 | Ramesh | |
| 7,149,737 B1 | 12/2006 | Luo et al. | |
| 7,478,080 B2 | 1/2009 | Pirahesh et al. | |
| 7,577,667 B2 | 8/2009 | Hinshaw et al. | |
| 7,617,179 B2 | 11/2009 | Nica | |
| 7,634,477 B2 | 12/2009 | Hinshaw | |
| 7,644,083 B1 | 1/2010 | Sirek | |
| 7,702,610 B2 * | 4/2010 | Zane | G06F 16/2448 707/999.001 |
| 7,761,477 B1 | 7/2010 | Luo et al. | |
| 7,882,100 B2 | 2/2011 | Andrei | |
| 8,001,110 B2 | 8/2011 | Hattori | |
| 8,055,651 B2 | 11/2011 | Barsness et al. | |
| 8,255,388 B1 | 8/2012 | Luo et al. | |
| 8,805,818 B2 | 8/2014 | Zane et al. | |
| 8,825,678 B2 | 9/2014 | Potapov et al. | |
| 8,949,834 B2 * | 2/2015 | Olston | G06F 16/951 718/102 |
| 9,183,256 B2 * | 11/2015 | Zane | G06F 16/2456 |
| 9,679,011 B2 | 6/2017 | Dixit et al. | |
| 10,019,481 B2 | 7/2018 | Jagtap et al. | |
| 10,380,112 B2 | 8/2019 | Bodziony et al. | |
| 10,397,317 B2 | 8/2019 | Balkesen et al. | |
| 2003/0065688 A1 | 4/2003 | Dageville et al. | |
| 2004/0172400 A1 * | 9/2004 | Zarom | G06F 16/90339 |
| 2004/0220923 A1 * | 11/2004 | Nica | G06F 16/24544 |
| 2006/0074901 A1 | 4/2006 | Pirahesh et al. | |
| 2006/0218123 A1 | 9/2006 | Chowdhuri et al. | |
| 2007/0073643 A1 | 3/2007 | Ghosh et al. | |
| 2008/0288473 A1 | 11/2008 | Hu et al. | |
| 2009/0228514 A1 * | 9/2009 | Liu | G06F 16/8365 |
| 2010/0131490 A1 | 5/2010 | Lamb et al. | |
| 2010/0205170 A1 | 8/2010 | Barsness et al. | |
| 2011/0252427 A1 * | 10/2011 | Olston | G06F 16/951 718/102 |
| 2011/0302151 A1 | 12/2011 | Abadi et al. | |
| 2012/0317094 A1 | 12/2012 | Bear et al. | |
| 2013/0117255 A1 | 5/2013 | Liu et al. | |
| 2013/0232133 A1 * | 9/2013 | Al-Omari | G06F 16/2456 707/714 |
| 2014/0006380 A1 | 1/2014 | Arndt et al. | |
| 2014/0280023 A1 | 9/2014 | Jagtap et al. | |
| 2015/0039852 A1 | 2/2015 | Sen et al. | |
| 2015/0039853 A1 | 2/2015 | Sen et al. | |
| 2015/0220600 A1 | 8/2015 | Bellamkonda | |
| 2015/0278306 A1 | 10/2015 | Cheng | |
| 2016/0098451 A1 | 4/2016 | Dickie | |
| 2019/0034486 A1 | 1/2019 | Bodziony et al. | |
| 2019/0104175 A1 | 4/2019 | Balkesen et al. | |
| 2019/0303370 A1 | 10/2019 | Bodziony et al. | |

* cited by examiner

ADAPTIVE DISTRIBUTION METHOD FOR HASH OPERATIONS

CROSS REFERENCE TO RELATED APPLICATIONS

This application is a continuation of U.S. application Ser. No. 16/858,510, filed Apr. 24, 2020, which is a continuation of U.S. application Ser. No. 16/039,710 entitled "Adaptive Distribution Method for Hash Operations," filed Jul. 19, 2018, which is a continuation of U.S. application Ser. No. 14/626,836, filed Feb. 19, 2015, entitled "Adaptive Distribution Method for Hash Operations," now U.S. Pat. No. 10,055,472, issued Aug. 21, 2018, which claims the benefit of U.S. Provisional Application Ser. No. 61/941,986, entitled "Apparatus and method for enterprise data warehouse data processing on cloud infrastructure," filed Feb. 19, 2014, the disclosure of which are incorporated herein by reference in its entirety.

TECHNICAL FIELD

The present disclosure relates to resource management systems and methods that manage data storage and computing resources.

BACKGROUND

Many existing data storage and retrieval systems are available today. For example, in a shared-disk system, all data is stored on a shared storage device that is accessible from all of the processing nodes in a data cluster. In this type of system, all data changes are written to the shared storage device to ensure that all processing nodes in the data cluster access a consistent version of the data. One of the main disadvantages of the shared link system is that as the number of processing nodes increases in a shared-disk system, the shared storage device (and the communication links between the processing nodes and the shared storage device) becomes a bottleneck that slows data read and data write operations. This bottleneck is further aggravated with the addition of more processing nodes. Thus, existing shared-disk systems have limited scalability due to this bottleneck problem.

Another existing data storage and retrieval system is referred to as a "shared-nothing architecture." In this architecture, data is distributed across multiple processing nodes such that each node stores a subset of the data in the entire database. When a new processing node is added or removed, the shared-nothing architecture must rearrange data across the multiple processing nodes. This rearrangement of data can be time-consuming and disruptive to data read and write operations executed during the data rearrangement. And, the affinity of data to a particular node can create "hot spots" on the data cluster for popular data. Further, since each processing node performs also the storage function, this architecture requires at least one processing node to store data. Thus, a disadvantage of the shared-nothing architecture is that it fails to store data if all processing nodes are removed. Additionally, management of data in a shared-nothing architecture is complex due to the distribution of data across many different processing nodes.

The systems and methods described herein provide an improved approach to data storage and data retrieval that alleviates the above-identified limitations of existing systems.

BRIEF DESCRIPTION OF THE DRAWINGS

Non-limiting and non-exhaustive embodiments of the present disclosure are described with reference to the following figures, wherein like reference numerals refer to like parts throughout the various figures unless otherwise specified.

DETAILED DESCRIPTION

Figure 1:
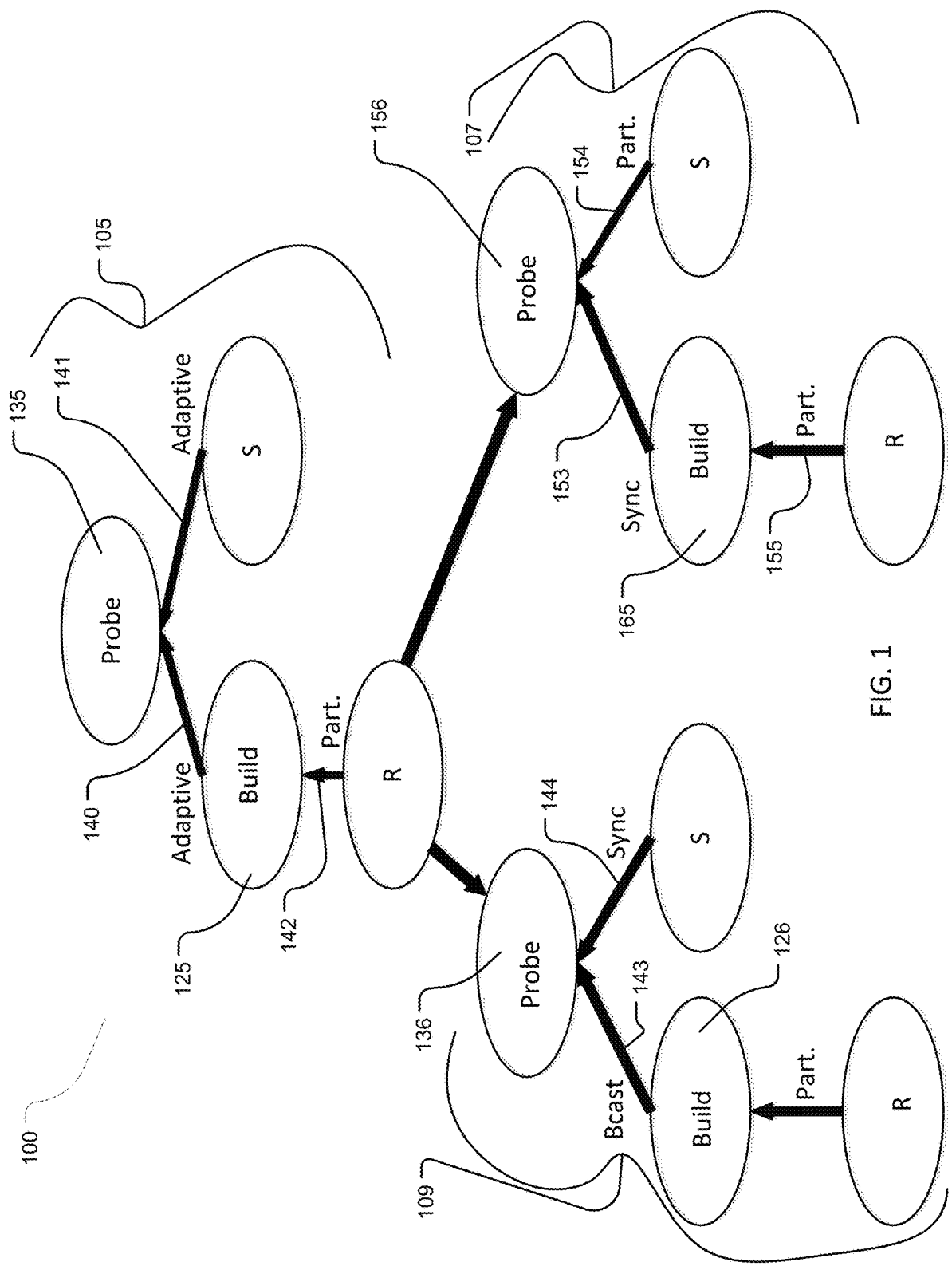
FIG. 1 illustrates a schematic of processes for joining a plurality of relations in accordance with the methods and systems described herein.

Disclosed herein are improved methods and systems for joining relations distributed over a computer network and associated via communication links and processing nodes. These methods and systems may reduce and/or eliminate the disadvantage of failing to store data if processing nodes are removed in the shared-nothing architecture, and the disadvantage of limited scalability in the shared-link system. Furthermore, the methods and systems described herein allow data to be stored and accessed as a service that may be separated from computing (or processing) resource considerations. The described methods and systems are useful with any type of data, and as discussed in greater detail below, these methods enable virtual warehouses to access any data to which it has access permissions, even at the same time as other virtual warehouses are accessing the same data. These disclosed methods and systems support running queries without any actual data stored in the local cache.

Additionally, the methods and systems described herein are capable of transparent dynamic data movement, which moves data from a remote storage device to a local cache, as needed, in a manner that is transparent to the user of the system. Further, this architecture supports data sharing without prior data movement since any virtual warehouse can access any data due to the decoupling of the data storage service from the computing service.

An exemplary method may begin by receiving a relational join query for a join operation comprising a predicate and a plurality of relations wherein the desired join uses an equivalence operation. Additionally, communication links between a build operation and a probe operation that may be substantially inactive are placed in an adaptive state, and communication links between a first relation and the probe operation that may be substantially inactive and are placed in an adaptive state. The method may further comprise placing communication links between a second relation in a partition state such that any tuples of the second relation are forwarded to the build operation, and repeating the build operation until the second relation is fully consumed and forwarded to the build operation such that an actual size of the second relation is known after being fully consumed. Additionally, the method may determine whether to join the relations via a broadcasting join or a re-portioning join based primarily on the actual size of the second relation, an estimated size of the first relation, and a cost metric.

In the following description, reference is made to the accompanying drawings that form a part thereof, and in which is shown by way of illustration specific exemplary embodiments in which the disclosure may be practiced. These embodiments are described in sufficient detail to enable those skilled in the art to practice the concepts disclosed herein, and it is to be understood that modifications to the various disclosed embodiments may be made, and other embodiments may be utilized, without departing from the scope of the present disclosure. The following detailed description is, therefore, not to be taken in a limiting sense.

Reference throughout this specification to "one embodiment," "an embodiment," "one example" or "an example" means that a particular feature, structure or characteristic described in connection with the embodiment or example is included in at least one embodiment of the present disclosure. Thus, appearances of the phrases "in one embodiment," "in an embodiment," "one example" or "an example" in various places throughout this specification are not necessarily all referring to the same embodiment or example. Furthermore, the particular features, structures, databases or characteristics may be combined in any suitable combinations and/or sub-combinations in one or more embodiments or examples. In addition, it should be appreciated that the figures provided herewith are for explanation purposes to persons ordinarily skilled in the art and that the drawings are not necessarily drawn to scale.

Embodiments in accordance with the present disclosure may be embodied as an apparatus, method or computer program product. Accordingly, the present disclosure may take the form of an entirely hardware-comprised embodiment, an entirely software-comprised embodiment (including firmware, resident software, micro-code, etc.) or an embodiment combining software and hardware aspects that may all generally be referred to herein as a "circuit," "module" or "system." Furthermore, embodiments of the present disclosure may take the form of a computer program product embodied in any tangible medium of expression having computer-usable program code embodied in the medium.

Any combination of one or more computer-usable or computer-readable media may be utilized. For example, a computer-readable medium may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present disclosure may be written in any combination of one or more programming languages. Such code may be compiled from source code to computer-readable assembly language or machine code suitable for the device or computer on which the code will be executed.

Embodiments may also be implemented in cloud computing environments. In this description and the following claims, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction and then scaled accordingly. A cloud model can be composed of various characteristics (e.g., on-demand self-service, broad network access, resource pooling, rapid elasticity, and measured service), service models (e.g., Software as a Service ("SaaS"), Platform as a Service ("PaaS"), and Infrastructure as a Service ("IaaS")), and deployment models (e.g., private cloud, community cloud, public cloud, and hybrid cloud).

The flow diagrams and block diagrams in the attached figures illustrate the architecture, functionality, and operation of possible implementations of systems, methods, and computer program products according to various embodiments of the present disclosure. In this regard, each block in the flow diagrams or block diagrams may represent a module, segment, or portion of code, which comprises one or more executable instructions for implementing the specified logical function(s). It will also be noted that each block of the block diagrams and/or flow diagrams, and combinations of blocks in the block diagrams and/or flow diagrams, may be implemented by special purpose hardware-based systems that perform the specified functions or acts, or combinations of special purpose hardware and computer instructions. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flow diagram and/or block diagram block or blocks.

The systems and methods described herein provide a flexible and scalable solution to the problem of computing a relational join in a distributed system in a manner that minimizes the amount of data to be copied, when the predicate θ contains at least one equality relation (making this a so-called equijoin), and when the size of input relations R and S is not known in advance. In some embodiments, the described systems and methods may leverage a cloud infrastructure that supports cloud-based storage resources, computing resources, and the like that will be described in greater detail below. Example cloud-based storage resources offer significant storage capacity available on-demand at a low cost. Further, these cloud-based storage resources may be fault-tolerant and highly scalable, which can be costly to achieve in private data storage systems.

In the described systems and methods, a data storage system may utilizes an SQL (Structured Query Language)-based relational database. However, these systems and methods are applicable to any type of database using any data storage architecture and using any language to store and retrieve data within the database. The systems and methods described herein further provide a multi-tenant system that supports isolation of distributed computing resources and data between different customers/clients and between different users within the same customer/client. In such systems in order to make the data useful, it may be evaluated through join processes which associate tuples for the relations that have been distributed over the system.

FIG. 1 illustrates a series of process for performing an equijoin of a plurality of relations in a distributed implementation. Assume we are computing an equijoin of two relations R and S. The figure shows three separate execution plans of processes that make up an equijoin. Relational operators and input expressions are represented as ovals, and communication links are represented as arrows, and the direction of the arrow indicates the direction of data flow. While the plan shows each operator as a single oval that may be part of a distributed execution plan. For each operator there are n instances, one instance for each process or machine in the system. These instances run in parallel and exchange data chiefly through communication links. In furtherance of the example implementation, let the input relations R and S be partitioned (i.e. fragmented) among the n processors or machines in the system. There are two basic ways to compute a distributed equijoin of R and S: broadcast one of the relations, or re-partition both input relations.

As used herein a join is a binary operator, taking at least two relations and a binary predicate as inputs from a user via a computer, and producing a single relation which contains the set of all combinations of tuples in the two relations which satisfy the predicate. To produce the correct result, any implementation of join associates all pairs of tuples which may satisfy the predicate. In a distributed implementation of a join, the system may copy tuples of the original relations over the network such that every corresponding pair of tuples is made available at one process, or on one computer within the system, which can then evaluate the predicate and produce a desired result of all tuples that satisfy the predicate.

As can be seen in the figure, relations R and S, and a binary predicate ($\theta$) may be received as inputs and processed into producing a single relation R Baa S which contains the set of all combinations of tuples in R and S which satisfy the predicate $\theta$. It should be noted that to produce the correct result, any implementation of must bring together all pairs of tuples which may satisfy the predicate $\theta$. In a distributed implementation of join, the system may therefore copy tuples of R and S over the networked system such that every corresponding pair of tuples becomes available to one process or machine within the system, which can then evaluate the predicate against the relations and discover all resultant tuples that satisfy the predicate.

As illustrated in the example, the input relations R and S may be stored (i.e. fragmented) among a plurality of processors or machines in a system. In an implementation a distributed equijoin of R and S may be computed by either broadcasting one of the relations over the network, or by re-partitioning both input relations into a single location within the system.

In a broadcasting join, one of the input relations (typically the smaller relation) is broadcast to n-number of processors or machines, while the other input relation (typically the larger relation) remains in situ. In the present implementation, |X| may represent the size of relation X in number of bytes, and relation R may be the relation that is broadcasted, therefore resulting in an expected asymptotic network cost of broadcast join that is represented by the expression $O(|R|*n)$.

In contrast, a re-partitioning join partitions the input relations according to one or more of the join keys (columns on which there exists an equality join predicate as part of the query). In certain embodiments, both hash partitioning or range partitioning may be applicable for this purpose. Each process or machine may be assigned one of the partitions, and the data of both input relations may then copied over the network accordingly. The expected asymptotic network cost of this re-partitioning is $O(|R|+|S|)$.

Additionally, one skilled in the art will recognize that deciding on which technique to apply, broadcast or re-partition, in order to minimize the network cost may be dependent on the size of the smaller input relation, say R. For example, if $|R|*n<|S|$, then a broadcast join may be preferred, otherwise a re-partitioning join is to be preferred.

It should be noted that network cost is just one metric to use for purposes of making a decision as to which join method is employed. In an implementation, a system may also take the memory cost and computational cost of the per-partition joins into account. It will be recognized by one skilled in the art that a broadcasting join replicates the broadcast relation at every process and it generally has higher memory and computational cost than a re-partitioning join.

The equijoin implementation may be split into two operators: build operators 125 and probe operators 135. The build operator 125 may be responsible for deciding whether to perform a broadcasting join or a re-partitioning join, while the probe operator 135 performs the actual, local join. A local join implementation may be orthogonal to this invention such that any local join implementation is possible such as for example: hash join, sort-merge join, and nested-loops. As used herein, a build operator typically builds a hash table while a probe operator reads the inner stream and probes the hash table to find matching rows in order to complete a hash join process. Additionally, as used herein an equijoin is an inner join statement or operation that uses an equivalence operation (i.e., colA=colB) to match rows from different tables, wherein an inner join statement requires each record in the joined relations to have matching records.

The upper plan 105 shows an execution plan at the beginning of query execution. The communication link 140 between the build operator and the probe operator, as well as communication link 141 between S and the probe operator, are initially inactive and in the "adaptive" state. The communication link 142 between R and the build operator is in the "partition" state, which means that any tuples produced by R are forwarded to one of the instances of the build operator, as determined by a partitioning function, such as a hash function over one or more of the columns of R which appear in equality predicates of the join predicate.

Initially, only the "left" side of the tree 105 in the figure may be executed; that is, the input relation R (which can be a base relation or itself the output of some complex sub-expression, for example another join) is fully consumed and forwarded to the build operator 125. One skilled in the art will understand that the build operator 125 may buffer all its input, either in main memory or on external storage (disk).

Once the relation R has been fully consumed by the build operator 125, the actual size of the relation R is known because the system knows the amount of data that has just been processed in the build operation. The system may then determine whether to perform a broadcasting or re-partitioning join based on the known-actual size of relation R, an estimated size of relation S, and a predetermined cost metric as discussed above.

It can be seen in FIG. 1 that the left lower execution plan 109 shows the plan for the broadcasting join, and the right lower execution plan 107 shows the plan for the re-partitioning join.

As illustrated, if the build operator decides to perform a broadcasting join, the link between the build operator and the probe operator is converted into a "bcast" (broadcast) link 143, and the link between relation S and the probe operator is converted to into a "sync" (synchronous) link. Then, it sends relation R through the broadcast link 143, which means the local partition of relation R of each instance of the build operator 126 is broadcasted to every instance of the probe operator 136. As used herein the terms "synchronous link" denote a local, one-to-one link between two operator instances, and does not cross machine or thread boundaries and can thus be implemented with relative efficiency. For example, a synchronous link may be a simple function call from the upstream operator's code into the downstream operator's code. In this implementation, a synchronous link does not perform a network transfer, and the local partition of relation S of each process or machine is directly forwarded to its local instance of the probe operator 136.

Conversely, if the build operator decides to perform a re-partitioning join, the communication link between the build operator 127 and the probe operator 137 is converted into a "sync" link 153, and converts the link between S and the probe operator into a partition or "part" link 154. Additionally, the partitioning function on relation S may be "compatible" with the partitioning function previously applied to relation R (in the communication link 155 between R and the build operator), such that each pair of tuples which may satisfy the predicate ends up in the same partition and thus at the same instance of the probe operator 156.

An important optimization to the re-partitioning example above, is that the build operator 165 instances need not read back their buffered input in order to send it over the "sync" link to their individually corresponding probe operator 156 instances. Relation R has already been re-partitioned by the communication link 155 between R and the build operator in a manner that is compatible with the "part." link 154 that is between S and the probe operator. Thus, the partition of relation R belonging to a corresponding build operator 165 instance can be passed whole without further processing. In some implementation the partition of relation R may be passed as a single pointer to a block of memory or a file on disk.

In contrast to existing products which rely on the query optimizer to make the decision on whether to broadcast or re-partition ahead of time, the present method describes a way to defer the decision on whether to broadcast or re-partition to query execution time; that is, to the point when the size of one of the input relations is known with certainty, and the size of the other input relation can often be estimated with greater accuracy. Thus, the present implementation provides a way to both determine the cost of a broadcasting join with a high level of certainty, and whether to make the decision to broadcast or re-partition relations with greater confidence.

These methods and processes may be immediately applicable to all implementations of distributed equijoin as found in virtually all distributed relational database systems, as well as implementations of equijoin in dataflow systems such as Hadoop/MapReduce. The above processes may be performed in a system having resource managers and multiple users.

Figure 2:
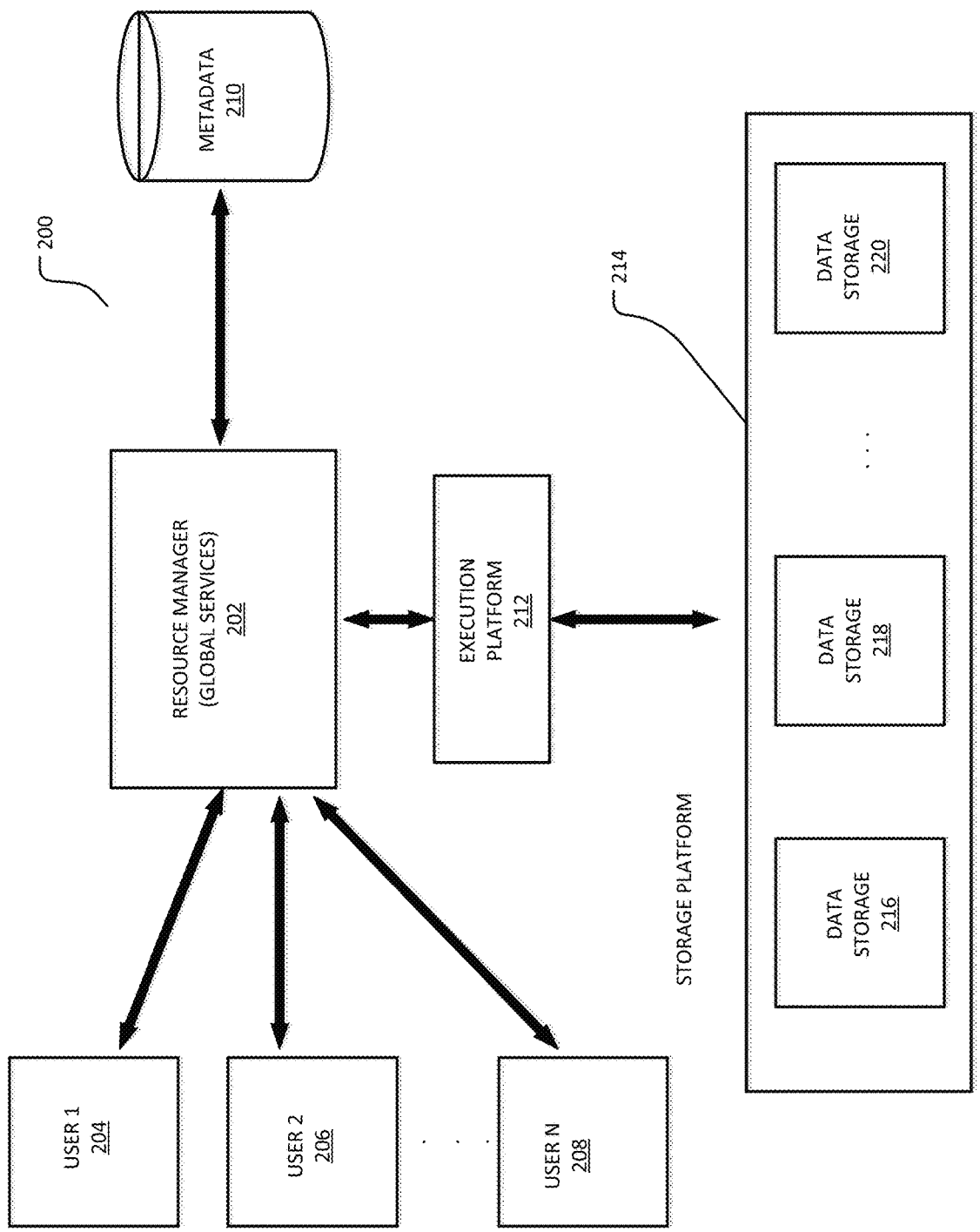
FIG. 2 illustrates a block diagram depicting an example embodiment of the systems and methods described herein.

As shown in FIG. 2, a resource manager 202 is coupled to multiple users 204, 206, and 208. In particular implementations, resource manager 202 can support any number of users desiring access to data processing platform 200. Users 204-208 may include, for example, end users providing data storage and retrieval requests, system administrators managing the systems and methods described herein, and other components/devices that interact with resource manager 202. Resource manager 202 provides various services and functions that support the operation of all systems and components within data processing platform 200. Resource manager 202 is also coupled to metadata 210, which is associated with the entirety of data stored throughout data processing platform 200. In some embodiments, metadata 210 includes a summary of data stored in remote data storage systems as well as data available from a local cache. Additionally, metadata 210 may include information regarding how data is organized in the remote data storage systems and the local caches. Metadata 210 allows systems and services to determine whether a piece of data needs to be processed without loading or accessing the actual data from a storage device.

Resource manager 202 is further coupled to an execution platform 212, which provides multiple computing resources that execute various data storage and data retrieval tasks, as discussed in greater detail below. Execution platform 212 is coupled to multiple data storage devices 216, 218, and 220 that are part of a storage platform 214. Although three data storage devices 216, 218, and 220 are shown in FIG. 2, execution platform 212 is capable of communicating with any number of data storage devices. In some embodiments, data storage devices 216, 218, and 220 are cloud-based storage devices located in one or more geographic locations. For example, data storage devices 216, 218, and 220 may be part of a public cloud infrastructure or a private cloud infrastructure. Data storage devices 216, 218, and 220 may be hard disk drives (HDDs), solid state drives (SSDs), storage clusters, Amazon S3™ storage systems or any other data storage technology. Additionally, storage platform 214 may include distributed file systems (such as Hadoop Distributed File Systems (HDFS)), object storage systems, and the like.

In particular embodiments, the communication links between resource manager 202 and users 204-208, metadata 210, and execution platform 212 are implemented via one or more data communication networks. Similarly, the communication links between execution platform 212 and data storage devices 216-220 in storage platform 214 are implemented via one or more data communication networks. These data communication networks may utilize any communication protocol and any type of communication medium. In some embodiments, the data communication networks are a combination of two or more data communication networks (or sub-networks) coupled to one another. In alternate embodiments, these communication links are implemented using any type of communication medium and any communication protocol.

As shown in FIG. 2, data storage devices 216, 218, and 220 are decoupled from the computing resources associated with execution platform 212. This architecture supports dynamic changes to data processing platform 200 based on the changing data storage/retrieval needs as well as the changing needs of the users and systems accessing data processing platform 200. The support of dynamic changes allows data processing platform 200 to scale quickly in response to changing demands on the systems and components within data processing platform 200. The decoupling of the computing resources from the data storage devices supports the storage of large amounts of data without requiring a corresponding large amount of computing resources. Similarly, this decoupling of resources supports a significant increase in the computing resources utilized at a particular time without requiring a corresponding increase in the available data storage resources.

Resource manager 202, metadata 210, execution platform 212, and storage platform 214 are shown in FIG. 2 as individual components. However, each of resource manager 202, metadata 210, execution platform 212, and storage platform 214 may be implemented as a distributed system (e.g., distributed across multiple systems/platforms at multiple geographic locations). Additionally, each of resource manager 102, metadata 110, execution platform 212, and storage platform 214 can be scaled up or down (independently of one another) depending on changes to the requests received from users 204-208 and the changing needs of data processing platform 200. Thus, in the described embodiments, data processing platform 100 is dynamic and supports regular changes to meet the current data processing needs.

Figure 3:
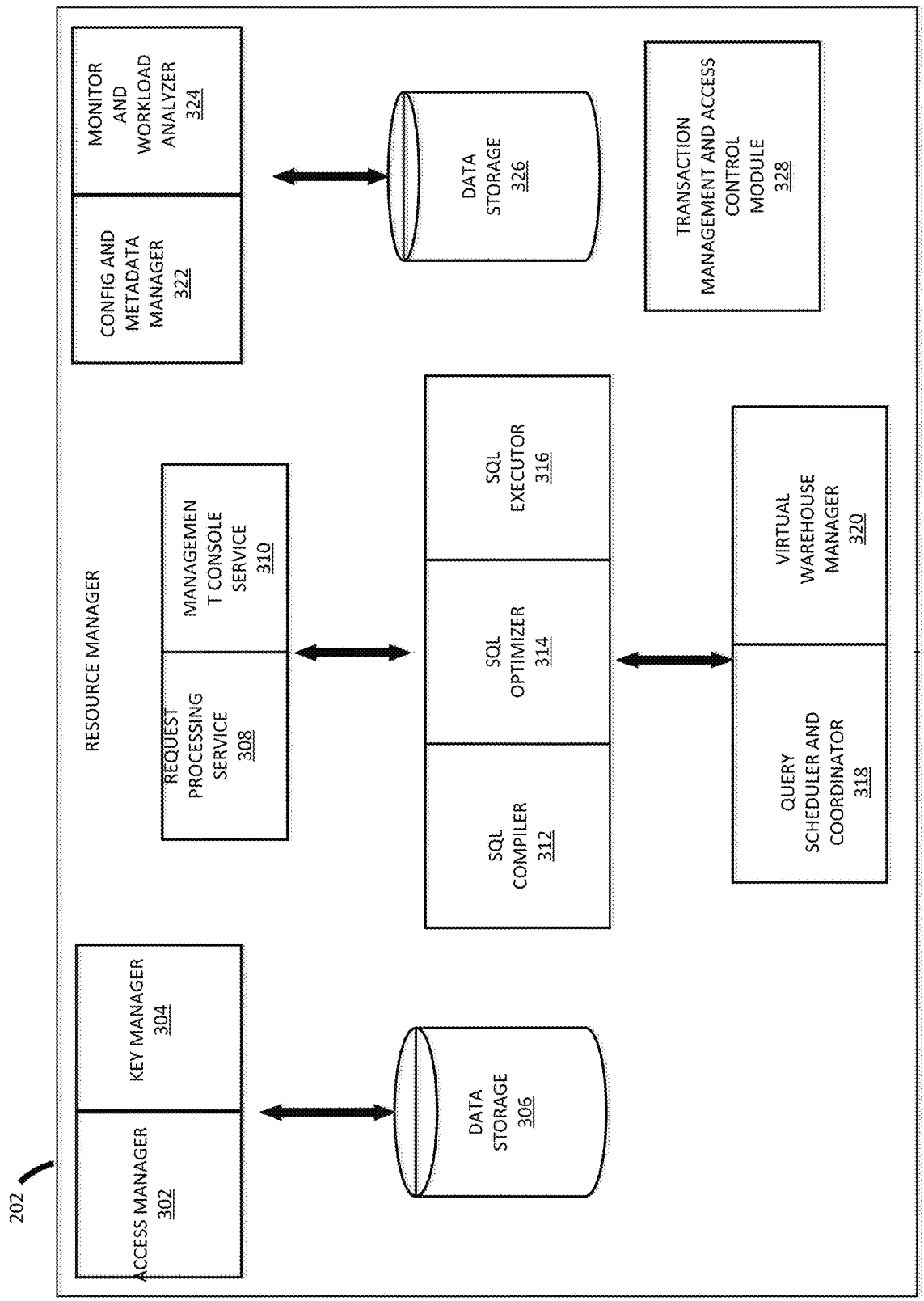
FIG. 3 illustrates a block diagram depicting an embodiment of a resource manager in accordance with the methods and systems described herein.

FIG. 3 illustrates a block diagram depicting an embodiment of resource manager 202. As shown in FIG. 3, resource manager 202 includes an access manager 302 and a key manager 304 coupled to a data storage device 306. Access manager 302 handles authentication and authorization tasks for the systems described herein. Key manager 304 manages storage and authentication of keys used during authentication and authorization tasks. A request processing service 308 manages received data storage requests and data retrieval requests. A management console service 310 supports access to various systems and processes by administrators and other system managers.

Resource manager 202 also includes an SQL compiler 312, an SQL optimizer 314 and an SQL executor 310. SQL compiler 312 parses SQL queries and generates the execution code for the queries. SQL optimizer 314 determines the best method to execute queries based on the data that needs to be processed. SQL executor 316 executes the query code for queries received by resource manager 302. A query scheduler and coordinator 318 sends received queries to the appropriate services or systems for compilation, optimization, and dispatch to execution platform 212. A virtual warehouse manager 320 manages the operation of multiple virtual warehouses implemented in execution platform 212.

Additionally, resource manager 202 includes a configuration and metadata manager 322, which manages the information related to the data stored in the remote data storage devices and in the local caches. A monitor and workload analyzer 324 oversees the processes performed by resource manager 102 and manages the distribution of tasks (e.g., workload) across the virtual warehouses and execution nodes in execution platform 212. Configuration and metadata manager 322 and monitor and workload analyzer 324 are coupled to a data storage device 326.

Resource manager 202 also includes a transaction management and access control module 328, which manages the various tasks and other activities associated with the processing of data storage requests and data access requests. For example, transaction management and access control module 328 provides consistent and synchronized access to data by multiple users or systems. Since multiple users/systems may access the same data simultaneously, changes to the data must be synchronized to ensure that each user/system is working with the current version of the data. Transaction management and access control module 328 provides control of various data processing activities at a single, centralized location in resource manager 202.

Figure 4:
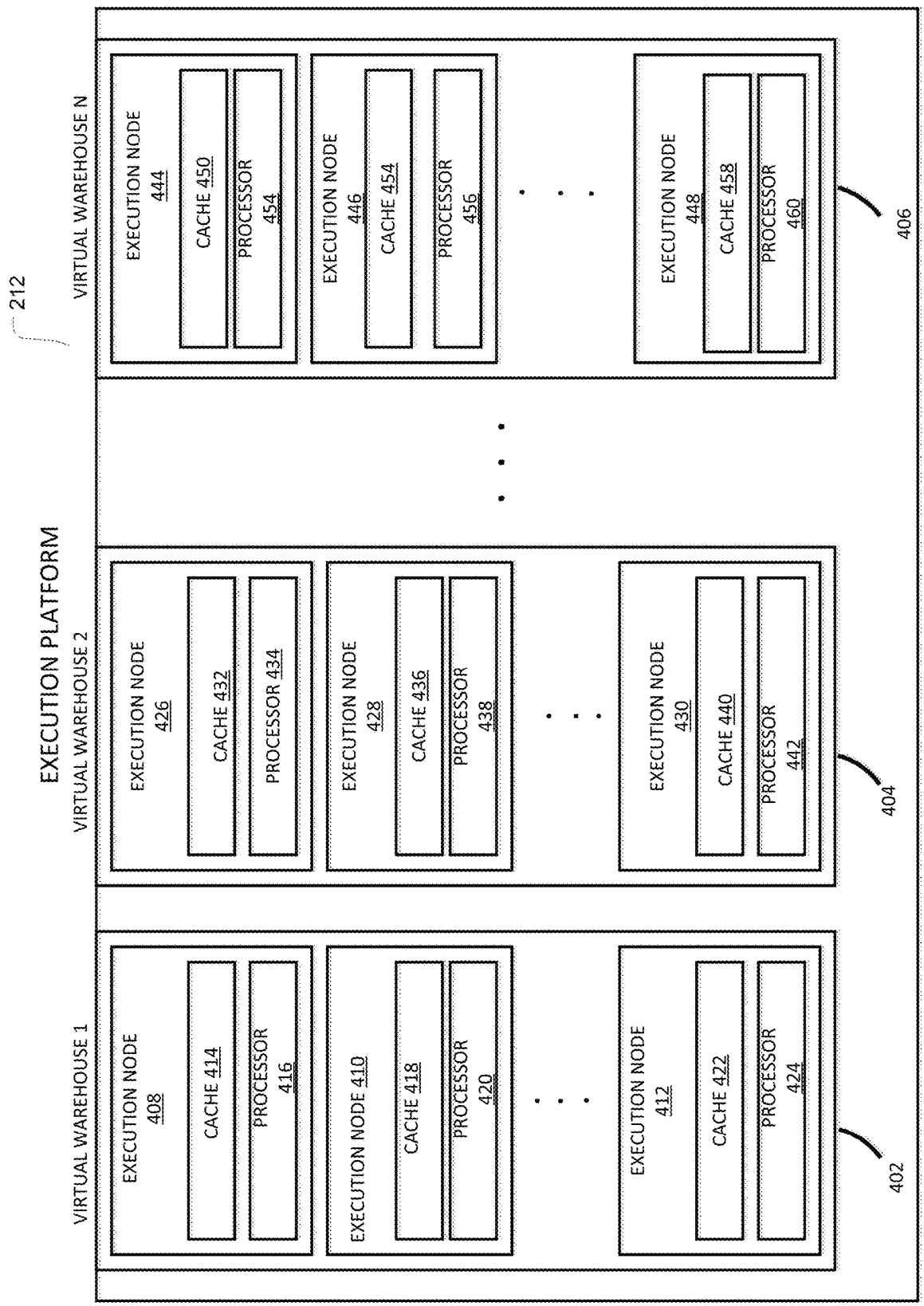
FIG. 4 illustrates a block diagram depicting an embodiment of an execution platform in accordance with the methods and systems described herein.

FIG. 4 is a block diagram depicting an embodiment of an execution platform 212 of FIG. 2 that is an example of a distributed system. As shown in FIG. 4, execution platform 212 includes multiple virtual warehouses 402, 404, and 406. Each virtual warehouse includes multiple execution nodes that each include a cache and a processor. Although each virtual warehouse 402-406 shown in FIG. 4 includes three execution nodes, a particular virtual warehouse may include any number of execution nodes. Further, the number of execution nodes in a virtual warehouse is dynamic, such that new execution nodes are created when additional demand is present, and existing execution nodes are deleted when they are no longer necessary.

Each virtual warehouse 402-406 is capable of accessing any of the data storage devices 216-220 shown in FIG. 2. Thus, virtual warehouses 402-406 are not necessarily assigned to a specific data storage device 216-220 and, instead, can access data from any of the data storage devices 216-220. Similarly, each of the execution nodes shown in FIG. 4 can access data from any of the data storage devices 216-220. In some embodiments, a particular virtual warehouse or a particular execution node may be temporarily assigned to a specific data storage device, but the virtual warehouse or execution node may later access data from any other data storage device.

In the example of FIG. 4, virtual warehouse 402 includes three execution nodes 408, 410, and 412. Execution node 408 includes a cache 414 and a processor 416. Execution node 410 includes a cache 418 and a processor 420. Execution node 412 includes a cache 422 and a processor 424. Each execution node 408-412 is associated with processing one or more data storage and/or data retrieval tasks. For example, a particular virtual warehouse may handle data storage and data retrieval tasks associated with a particular user or customer. In other implementations, a particular virtual warehouse may handle data storage and data retrieval tasks associated with a particular data storage system or a particular category of data.

Similar to virtual warehouse 402 discussed above, virtual warehouse 404 includes three execution nodes 426, 428, and 430. Execution node 426 includes a cache 432 and a processor 434. Execution node 428 includes a cache 436 and a processor 438. Execution node 430 includes a cache 440 and a processor 442. Additionally, virtual warehouse 406 includes three execution nodes 444, 446, and 448. Execution node 444 includes a cache 450 and a processor 452. Execution node 446 includes a cache 454 and a processor 456. Execution node 448 includes a cache 458 and a processor 460.

Although the execution nodes shown in FIG. 4 each include one cache and one processor, alternate embodiments may include execution nodes containing any number of processors and any number of caches. Additionally, the caches may vary in size among the different execution nodes. The caches shown in FIG. 4 store, in the local execution node, data that was retrieved from one or more data storage devices in storage platform 214 (FIG. 2). Thus, the caches reduce or eliminate the bottleneck problems occurring in platforms that consistently retrieve data from remote storage systems. Instead of repeatedly accessing data from the remote storage devices, the systems and methods described herein access data from the caches in the execution nodes which is significantly faster and avoids the bottleneck problem discussed above. In some embodiments, the caches are implemented using high-speed memory devices that provide fast access to the cached data. Each cache can store data from any of the storage devices in storage platform 214.

Further, the cache resources and computing resources may vary between different execution nodes. For example, one execution node may contain significant computing resources and minimal cache resources, making the execution node useful for tasks that require significant computing resources. Another execution node may contain significant cache resources and minimal computing resources, making this execution node useful for tasks that require caching of large amounts of data. In some embodiments, the cache resources and computing resources associated with a particular execution node are determined when the execution node is created, based on the expected tasks to be performed by the execution node.

Additionally, the cache resources and computing resources associated with a particular execution node may change over time based on changing tasks performed by the execution node. For example, a particular execution node may be assigned more processing resources if the tasks performed by the execution node become more processor intensive. Similarly, an execution node may be assigned more cache resources if the tasks performed by the execution node require a larger cache capacity.

Although virtual warehouses 402-406 are associated with the same execution platform 212, the virtual warehouses may be implemented using multiple computing systems at multiple geographic locations. For example, virtual warehouse 402 can be implemented by a computing system at a first geographic location, while virtual warehouses 404 and 406 are implemented by another computing system at a second geographic location. In some embodiments, these different computing systems are cloud-based computing systems maintained by one or more different entities.

Additionally, each virtual warehouse is shown in FIG. 4 as having multiple execution nodes. The multiple execution nodes associated with each virtual warehouse may be implemented using multiple computing systems at multiple geographic locations. For example, a particular instance of virtual warehouse 402 implements execution nodes 408 and 410 on one computing platform at a particular geographic location, and implements execution node 412 at a different computing platform at another geographic location. Selecting particular computing systems to implement an execution node may depend on various factors, such as the level of resources needed for a particular execution node (e.g., processing resource requirements and cache requirements), the resources available at particular computing systems, communication capabilities of networks within a geographic location or between geographic locations, and which computing systems are already implementing other execution nodes in the virtual warehouse. Execution platform 212 is also fault tolerant. For example, if one virtual warehouse fails, that virtual warehouse is quickly replaced with a different virtual warehouse at a different geographic location.

A particular execution platform 212 may include any number of virtual warehouses 402-406. Additionally, the number of virtual warehouses in a particular execution platform is dynamic, such that new virtual warehouses are created when additional processing and/or caching resources are needed. Similarly, existing virtual warehouses may be deleted when the resources associated with the virtual warehouse are no longer necessary.

Figure 5:
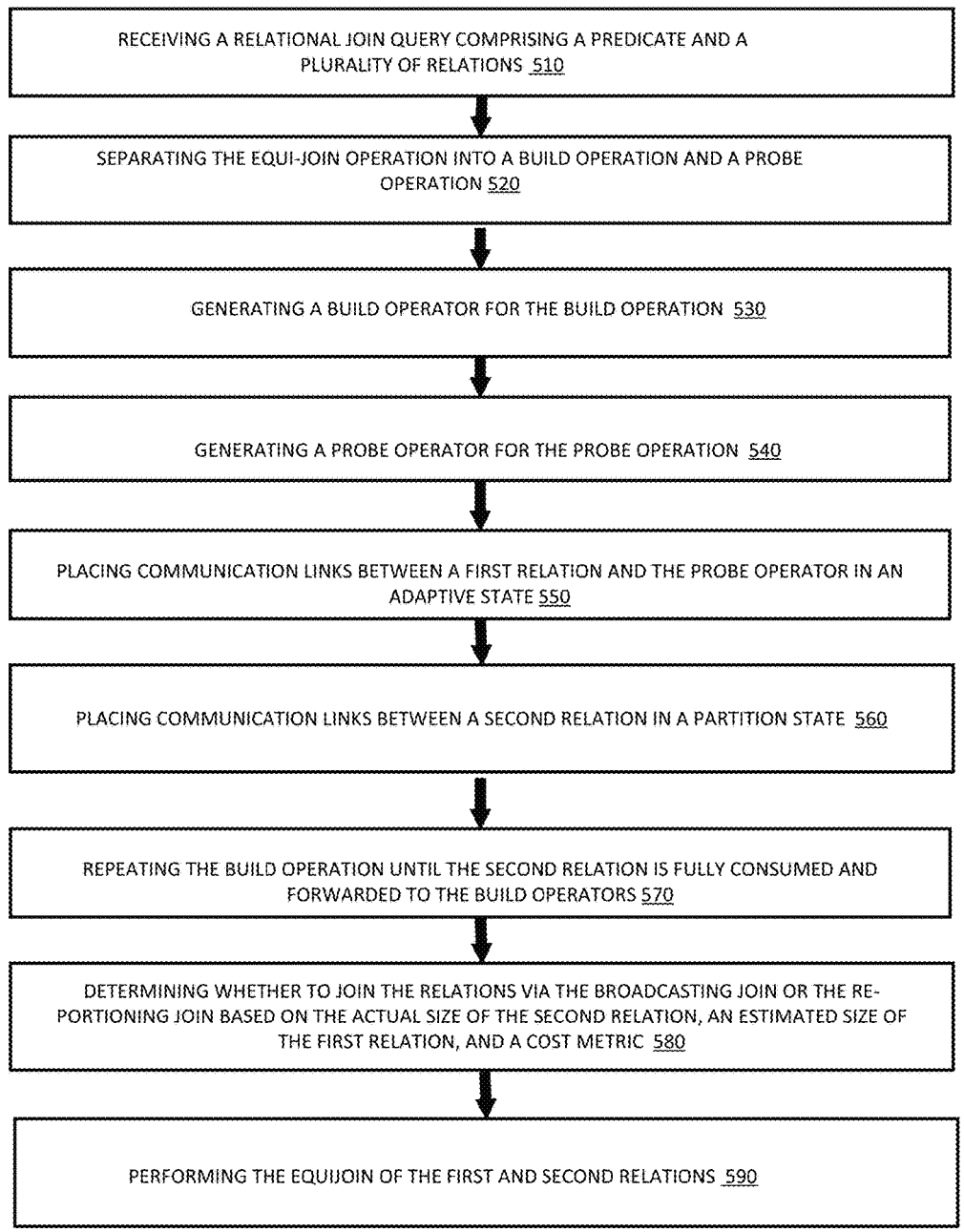
FIG. 5 illustrates a method for the join of a plurality of relations in accordance with the methods and systems described herein.

FIG. 5 illustrates an implementation of a method for performing a equijoin process over a distributed system. As can be seen in the figure, method 500 may begin with receiving a relational join query comprising a predicate and a plurality of relations at 510. As in the example of FIG. 1, the first and second relations may be R and S. As illustrated in FIG. 1, the input relations R and S may be stored among a plurality of processors or machines in a system. In an implementation a distributed equijoin of R and S may be computed by either broadcasting one of the relations over the network, or by re-partitioning both input relations into a single location within the system.

The method may then call for separating the equijoin operation into a build operation and a probe operation 520, and will continue by generating a build operator for the build operation at 530 and a probe operator for the probe operations at 540. The build operator may be responsible for deciding whether to perform broadcasting or re-partitioning join, and the probe operator may perform the actual, local join. In an implementation the local join implementation may be orthogonal to this invention such that any local join implementation is possible such as for example: hash join, sort-merge join, and nested-loops.

Once the probe operator and build operator has been created, the method 500 can address the communication links to the relations by placing communication links between a first relation and the probe operator in an adaptive state at 550. In an implementation, the adaptive state may be a waiting state that will later be modified into an active state during execution of the method. For example, the communication link between the build operator and the probe operator, as well as communication link between S and the probe operator, are initially inactive and in the "adaptive" state.

The method may then continue by placing the communication links to a second relation, in a partition state at 560, wherein the partition state facilitates the partition move of the second relation. For example, the communication link between R and the build operator may be in the "part." state, which means that any tuples produced by R are forwarded to one of the instances of the build operator, as determined by a partitioning function, such as a hash function over one or more of the columns of R which appear in equality predicates of the join predicate.

Once the communication links are place in the proper state, at 570 the method causes computing components within the system to repeat the build operation until the second relation is fully consumed and forwarded to the build operators. As mentioned above, the build operators may be stored in local cache so as to reduce traffic over the distributed system. After the relation has been consumed by the build operator the actual size of the relation is known. Having actual knowledge of the relation allows the method to determine the most efficient type of join to use.

Accordingly, at 580 the method determines whether to join the relations via the broadcasting join or the re-portioning join based on the actual size of the second relation, an estimated size of the first relation, and a cost metric. Additionally, one skilled in the art will recognize, that deciding on which technique to apply, broadcast or re-partition, in order to minimize the network cost may be dependent on the size of the smaller input relation, say R. For example, if $|R|*n<|R|+|S|$, then a broadcast join may be preferred, otherwise a re-partitioning join is to be preferred. It should be noted that network cost is just one metric to use for purposes of making a decision as to which join method is employed. In an implementation, a system may also take the memory cost and computational cost of the per-partition joins into account. It will be recognized by one skilled in the art that a broadcasting join replicates the broadcast relation at every process and it generally has higher memory and computational cost than a re-partitioning join.

At 590, the method causes the computing components of the system to perform the equijoin of the first and second relations, thereby returning all of the tuples that satisfy the predicate. As used herein a join is a binary operator, taking at least two relations and a binary predicate as inputs from a user via a computer, and producing a single relation which contains the set of all combinations of tuples in the two relations which satisfy the predicate. To produce the correct result, any implementation of join associates all pairs of tuples which may satisfy the predicate. In a distributed implementation of a join, the system may copy tuples of the original relations over the network such that every corresponding pair of tuples is made available at one process, or on one computer within the system, which can then evaluate the predicate and produce a desired result of all tuples that satisfy the predicate.

Figure 6:
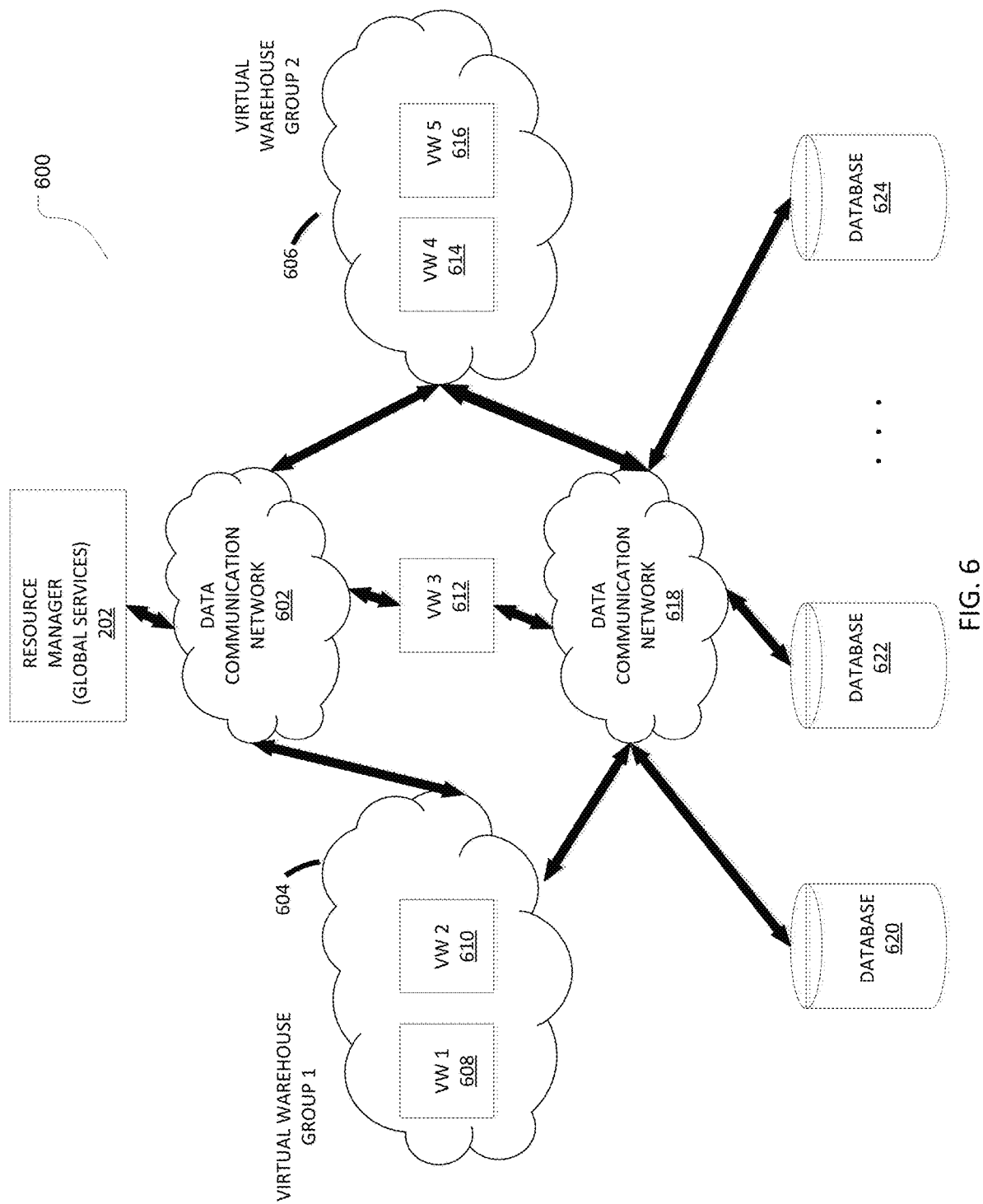
FIG. 6 illustrates a block diagram depicting an example operating environment having multiple distributed virtual warehouses and virtual warehouse groups in accordance with the methods and systems described herein.

FIG. 6 is a block diagram depicting another example operating environment 600 having multiple distributed virtual warehouses and virtual warehouse groups. Environment 600 includes resource manager 202 that communicates with virtual warehouse groups 604 and 606 through a data communication network 602. Warehouse group 604 includes two virtual warehouses 608 and 610, and warehouse group 606 includes another two virtual warehouses 614 and 616. Resource manager 202 also communicates with virtual warehouse 612 (which is not part of a virtual warehouse group) through data communication network 602.

Virtual warehouse groups 604 and 606 as well as virtual warehouse 612 communicate with databases 620, 622, and 624 through a data communication network 618. In some embodiments data communication networks 602 and 618 are the same network. Environment 600 allows resource manager 202 to coordinate user data storage and retrieval requests across the multiple virtual warehouses 608-616 to store and retrieve data in databases 620-624. Virtual warehouse groups 604 and 606 can be located in the same geographic area, or can be separated geographically. Additionally, virtual warehouse groups 604 and 606 can be implemented by the same entity or by different entities.

The systems and methods described herein allow data to be stored and accessed as a service that is separate from computing (or processing) resources. Even if no computing resources have been requested from the execution platform, data is available to a virtual warehouse without requiring reloading of the data from a remote data source. The described systems and methods are useful with any type of data. In particular embodiments, data is stored in a structured, optimized format. The decoupling of the data storage/access service from the computing services also simplifies the sharing of data among different users and groups. As discussed herein, each virtual warehouse can access any data to which it has access permissions, even at the same time as other virtual warehouses are accessing the same data. This architecture supports running queries without any actual data stored in the local cache. The systems and methods described herein are capable of transparent dynamic data movement, which moves data from a remote storage device to a local cache, as needed, in a manner that is transparent to the user of the system. Further, this architecture supports data sharing without prior data movement since any virtual warehouse can access any data due to the decoupling of the data storage service from the computing service.

Figure 7:
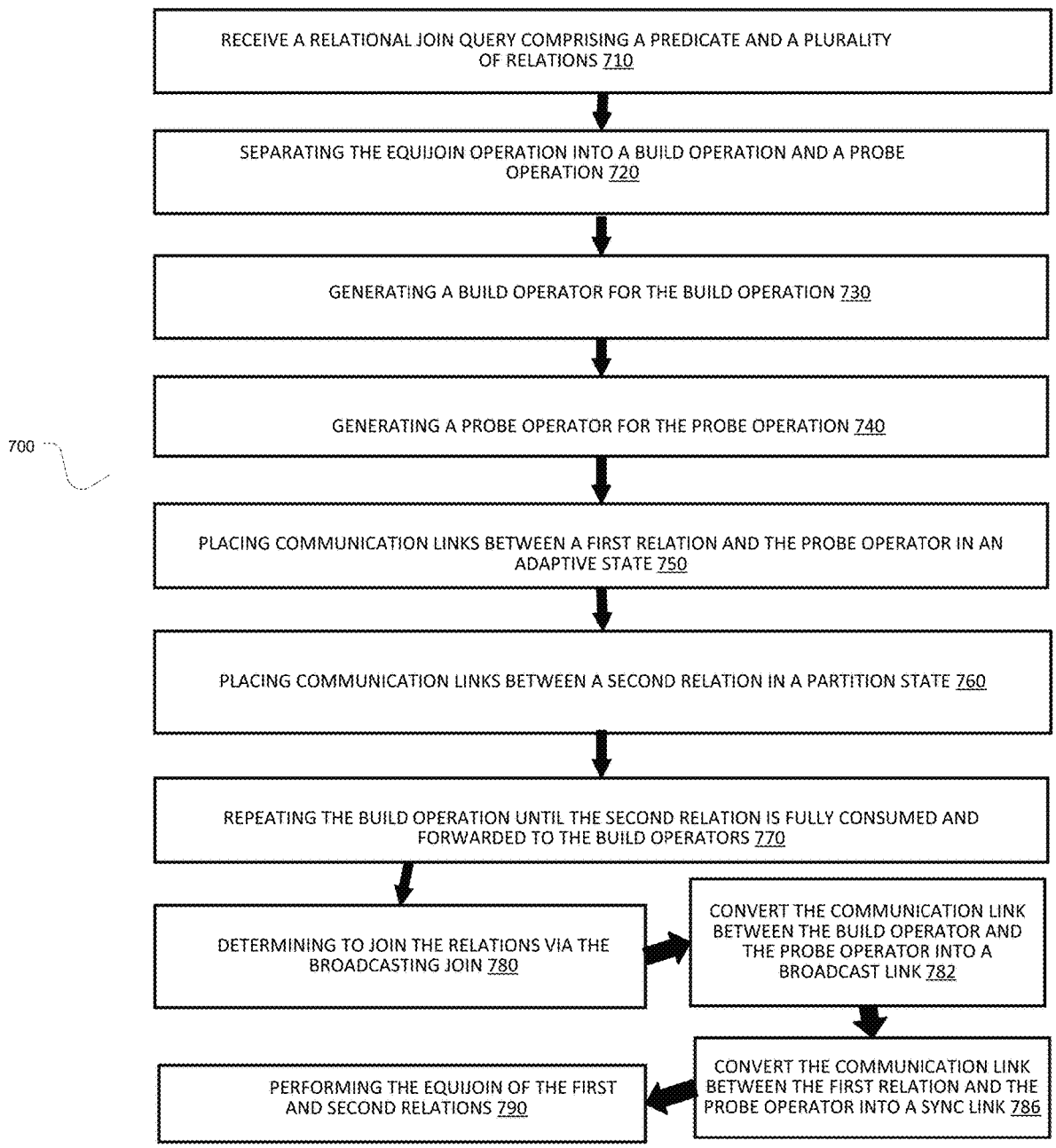
FIG. 7 illustrates a flow diagram depicting an embodiment of a method for a join of a plurality of relations in accordance with the methods and systems described herein.

FIG. 7 illustrates an implementation of a method for performing a join process over a distributed system wherein a broadcast join has been determined to be the optimal join. As can be seen in the figure, method 700 may begin with receiving a relational join query comprising a predicate and a plurality of relations at 710.

The method may then call for separating the equijoin operation into a build operation and a probe operation 720, and will continue by generating a build operator for the build operation at 730 and a probe operator for the probe operations at 740. In the implementation the build operator may be responsible for deciding whether to perform broadcasting or re-partitioning join, and the probe operator may perform the actual, local join.

Once the probe operator and build operator has been created, the method 700 can address the communication links to the relations by placing communication links between a first relation and the probe operator in an adaptive state at 750. In an implementation, the communication link between the first relation (S) and the probe operator, may be initially inactive and in the "adaptive" state.

The method may then continue by placing the communication links to a second relation, in a partition state at 760, wherein the partition state facilitates the partition move of the second relation.

Once the communication links are place in the proper state, at 770 the method causes computing components within the system to repeat the build operation until the second relation is fully consumed and forwarded to the build operators. As mentioned above, the build operators may be stored in local cache so as to reduce traffic over the distributed system. After the relation has been consumed by the build operator the exact or actual size of the relation is known. Having actual knowledge of the relation allows the method to determine the most efficient type of join to continue with.

In the implementation, at 780 the method determines to join the relations via the broadcasting join based on the actual size of the second relation, an estimated size of the first relation, and a cost metric. At 782, the method converts the communication link between the build operator and the probe operator into a broadcast link to facilitate the broadcast join. Then the method sends the corresponding relation through the broadcast link, which means the local partition of the relation of each instance of the build operator is broadcasted to every instance of the probe operator.

Additionally, at 786 the method converts the communication link between the first relation and the probe operator into a sink link. In this implementation, a synchronous link does not perform a network transfer. In other words, the local partition of the relation of each process or machine is directly forwarded to its local instance of the probe operator.

At 790, the method causes the computing components of the system to perform the equijoin of the first and second relations, thereby returning all of the tuples that satisfy the predicate.

Figure 8:
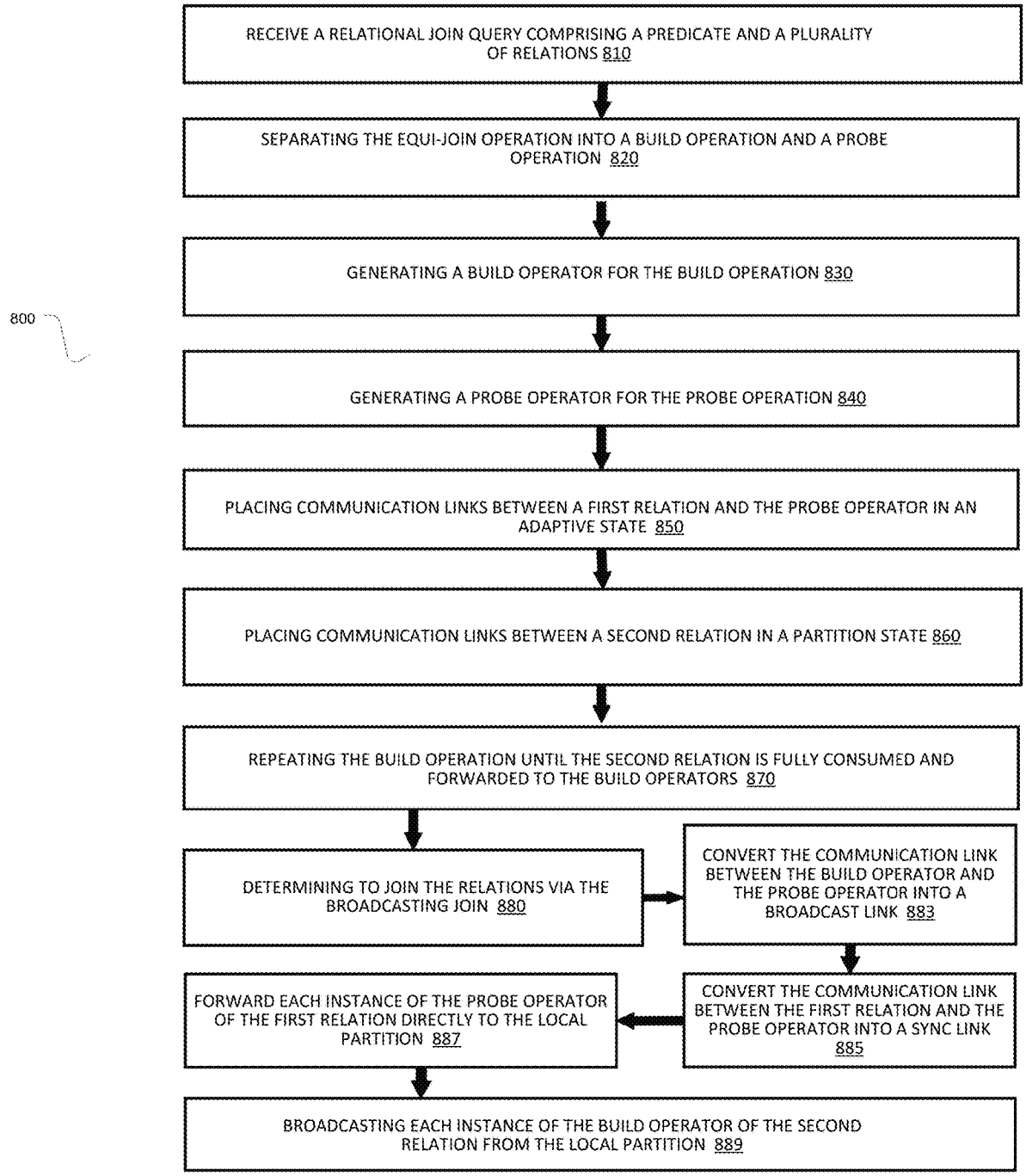
FIG. 8 illustrates a flow diagram depicting an embodiment of a method for a join of a plurality of relations in accordance with the methods and systems described herein.

FIG. 8 illustrates an implementation of a method for performing a join process over a distributed system wherein a partition join has been determined to be the optimal join. As can be seen in the figure, method 800 may begin with receiving a relational join query comprising a predicate and a plurality of relations at 810.

The method may then call for separating the equijoin operation into a build operation and a probe operation 820, and will continue by generating a build operator for the build operation at 830 and a probe operator for the probe operations at 840. In the implementation the build operator may be responsible for deciding whether to perform broadcasting or re-partitioning join, and the probe operator may perform the actual, local join.

Once the probe operator and build operator has been created, the method 800 can address the communication links to the relations by placing communication links between a first relation and the probe operator in an adaptive state at 850. In an implementation, the communication link between the first relation and the probe operator, may be initially inactive and in the "adaptive" state.

The method may then continue by placing the communication links to a second relation, in a partition state at 860, wherein the partition state facilitates the partition move of the second relation.

Once the communication links are place in the proper state, at 870 the method causes computing components within the system to repeat the build operation until the second relation is fully consumed and forwarded to the build operators. As mentioned above, the build operators may be stored in local cache so as to reduce traffic over the distributed system. After the relation has been consumed by the build operator the exact or actual size of the relation is known. Having actual knowledge of the relation allows the method to determine the most efficient type of join to continue with.

In the implementation, at 880 the method determines to join the relations via the repartitioning join based on the actual size of the second relation, an estimated size of the first relation, and a cost metric. At 883, the method converts the communication link between the build operator and the probe operator into a broadcast link. Then the method sends the corresponding relation through the partition link Additionally, at 885 the method converts the communication link between the first relation and the probe operator into a synchronous link. In this implementation, a synchronous link does not perform a network transfer.

At 887, the relation of each process or machine is directly forwarded to its local instance of the probe operator. Additionally, at 889 the method broadcasts each instance of the build operator of the second relation from the local partition and thereby causes the computing components of the system to perform the repartition equijoin of the first and second relations, thereby returning all of the tuples that satisfy the predicate.

Figure 9:
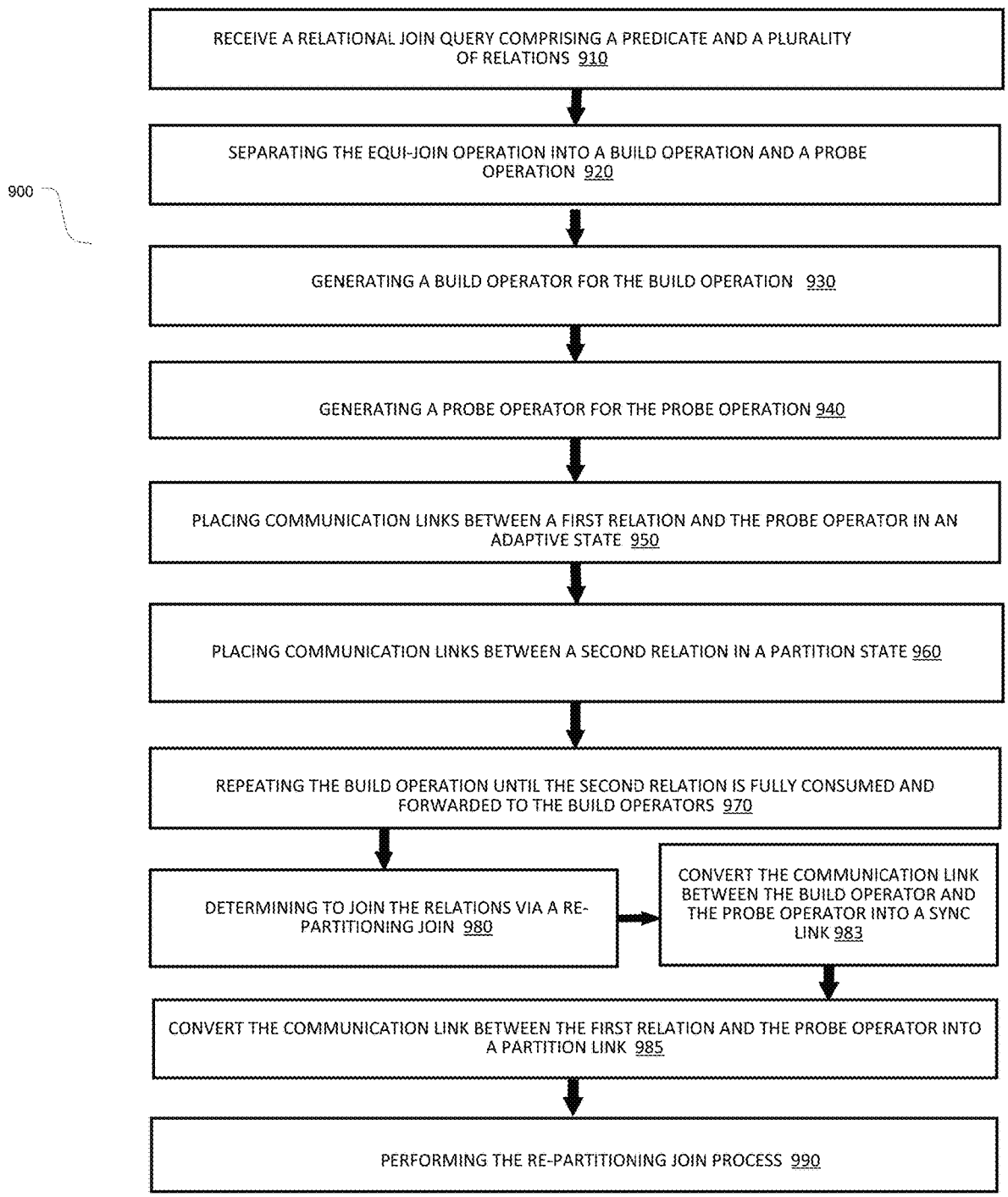
FIG. 9 illustrates a flow diagram depicting an embodiment of a method for a join of a plurality of relations in accordance with the methods and systems described herein.

FIG. 9 illustrates an implementation of a method for performing a join process over a distributed system wherein a partition join has been determined to be the optimal join. As can be seen in the figure, method 900 may begin with receiving a relational join query comprising a predicate and a plurality of relations at 910.

The method may then call for separating the equijoin operation into a build operation and a probe operation 920, and will continue by generating a build operator for the build operation at 930 and a probe operator for the probe operations at 940. In the implementation the build operator may be responsible for deciding whether to perform broadcasting or re-partitioning join, and the probe operator may perform the actual, local join.

Once the probe operator and build operator has been created, the method 900 can address the communication links to the relations by placing communication links between a first relation and the probe operator in an adaptive state at 950. In an implementation, the communication link between the first relation and the probe operator, may be initially inactive and in the "adaptive" state.

The method may then continue by placing the communication links to a second relation, in a partition state at 960, wherein the partition state facilitates the partition move of the second relation.

Once the communication links are place in the proper state, at 970 the method causes computing components within the system to repeat the build operation until the second relation is fully consumed and forwarded to the build operators. As mentioned above, the build operators may be stored in local cache so as to reduce traffic over the distributed system. After the relation has been consumed by the build operator the exact or actual size of the relation is known. Having actual knowledge of the relation allows the method to determine the most efficient type of join to continue with.

In the implementation, at 980 the method determines to join the relations via the repartitioning join based on the actual size of the second relation, an estimated size of the first relation, and a cost metric. At 983, the method converts the communication link between the build operator and the probe operator into a synchronous link.

Additionally, at 985 the method converts the communication link between the first relation and the probe operator into a partition link.

At 990, the local partition of the relation of each process or machine is directly forwarded to its local instance of the probe operator in order to perform the repartition equijoin of the first and second relations, thereby returning all of the tuples that satisfy the predicate.

Figure 10:
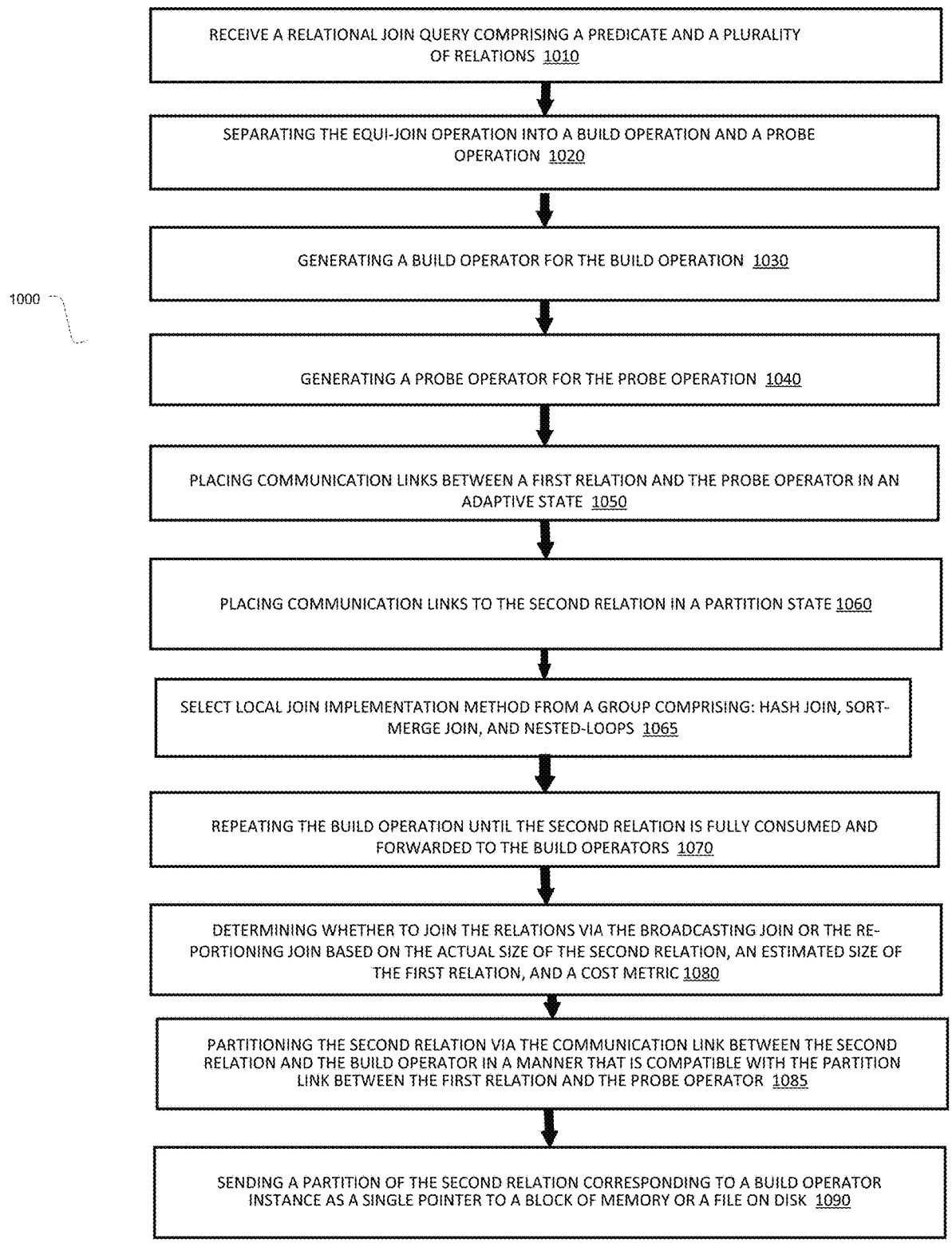
FIG. 10 illustrates a flow diagram depicting an embodiment of a method for a join of a plurality of relations in accordance with the methods and systems described herein.

FIG. 10 illustrates an implementation of a method for performing a join process over a distributed system. As can be seen in the figure, method 1000 may begin with receiving a relational join query comprising a predicate and a plurality of relations at 1010.

The method may then call for separating the equijoin operation into a build operation and a probe operation 1020, and will continue by generating a build operator for the build operation at 1030 and a probe operator for the probe operations at 1040. In the implementation the build operator may be responsible for deciding whether to perform broadcasting or re-partitioning join, and the probe operator may perform the actual, local join.

Once the probe operator and build operator have been created, the method 1000 can address the communication links to the relations by placing communication links between a first relation and the probe operator in an adaptive state at 1000. In an implementation, the communication link between the first relation and the probe operator, may be initially inactive and in the "adaptive" state.

The method may then continue by converting the communication links to the second relation from an adaptive state in to a partition state at 1060. The method may then select an optimal processing method at 1065 from a group comprising the methods: hash join, sort-merge join, and nested-loops in order to accomplish the join optimally.

At 1070 the method causes computing components within the system to repeat the build operation until the second relation is fully consumed and forwarded to the build operators. After the relation has been consumed by the build operator the actual size of the relation is known. Having actual knowledge of the relation allows the method to determine the most efficient type of join to continue with.

In the implementation, at 1080 the method determines to join the relations via the repartitioning join based on the actual size of the second relation, an estimated size of the first relation, and a cost metric. At 1085, the method may call for the partitioning of the second relation via the communication link between the second relation and the build operator in a manner that is compatible with the partition link between the first relation and the probe.

At 1090, the method may send a partition of the second relation corresponding to a build operator instance as a single pointer to a block of memory or a file on disk in order to complete the join operation.

It should be noted that a second relation may be a base relation, or may be an output of a sub-expression. Additionally, all of the above operators may buffer to main memory or external storage.

Figure 11:
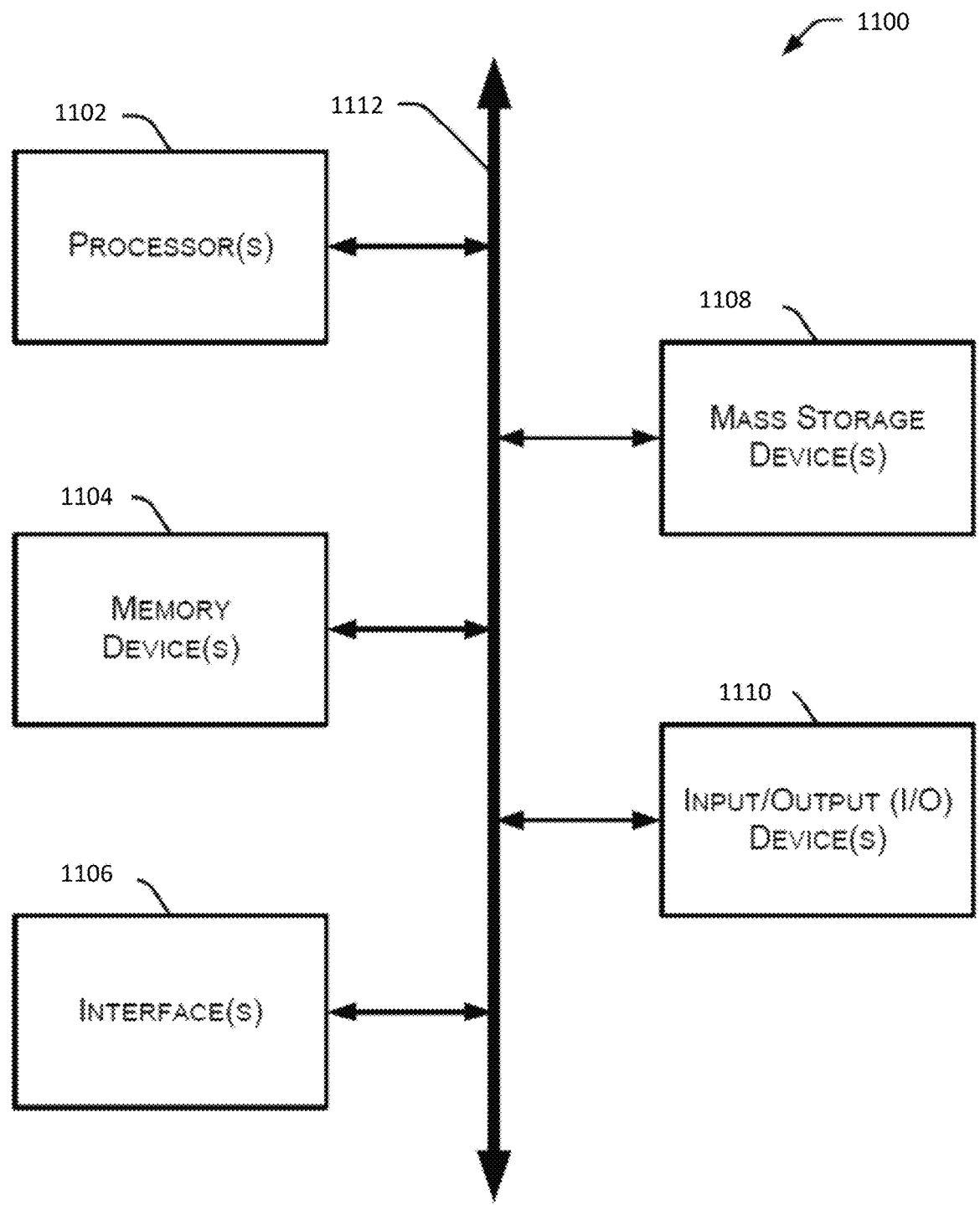
FIG. 11 illustrates a block diagram depicting an example computing device in accordance with the methods and systems described herein.

FIG. 11 is a block diagram depicting an example computing device 1100. In some embodiments, computing device 1100 is used to implement one or more of the systems and components discussed herein. For example, computing device 1100 may allow a user or administrator to access resource manager 202. Further, computing device 1100 may interact with any of the systems and components described herein. Accordingly, computing device 1100 may be used to perform various procedures and tasks, such as those discussed herein. Computing device 1100 can function as a server, a client or any other computing entity. Computing device 1100 can be any of a wide variety of computing devices, such as a desktop computer, a notebook computer, a server computer, a handheld computer, a tablet, and the like.

Computing device 1100 includes one or more processor(s) 1102, one or more memory device(s) 1104, one or more interface(s) 1106, one or more mass storage device(s) 1108, and one or more Input/Output (I/O) device(s) 1110, all of which are coupled to a bus 1112. Processor(s) 1102 include one or more processors or controllers that execute instructions stored in memory device(s) 1104 and/or mass storage device(s) 1108. Processor(s) 1102 may also include various types of computer-readable media, such as cache memory.

Memory device(s) 1104 include various computer-readable media, such as volatile memory (e.g., random access memory (RAM)) and/or nonvolatile memory (e.g., read-only memory (ROM)). Memory device(s) 1104 may also include rewritable ROM, such as Flash memory.

Mass storage device(s) 1108 include various computer readable media, such as magnetic tapes, magnetic disks, optical disks, solid state memory (e.g., Flash memory), and so forth. Various drives may also be included in mass storage device(s) 1108 to enable reading from and/or writing to the various computer readable media. Mass storage device(s) 1108 include removable media and/or non-removable media.

I/O device(s) 1110 include various devices that allow data and/or other information to be input to or retrieved from computing device 1100. Example I/O device(s) 1110 include cursor control devices, keyboards, keypads, microphones, monitors or other display devices, speakers, printers, network interface cards, modems, lenses, CCDs or other image capture devices, and the like.

Interface(s) 1106 include various interfaces that allow computing device 1100 to interact with other systems, devices, or computing environments. Example interface(s) 1106 include any number of different network interfaces, such as interfaces to local area networks (LANs), wide area networks (WANs), wireless networks, and the Internet.

Bus 1112 allows processor(s) 1102, memory device(s) 1104, interface(s) 1106, mass storage device(s) 1108, and I/O device(s) 1110 to communicate with one another, as well as other devices or components coupled to bus 1112. Bus 1112 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 1100, and are executed by processor(s) 1102. Alternatively, the systems and procedures described herein can be implemented in hardware, or a combination of hardware, software, and/or firmware. For example, one or more application specific integrated circuits (ASICs) can be programmed to carry out one or more of the systems and procedures described herein. Additionally, as used herein, a "module" is intended to mean any combination of software, computer hardware, and firmware that operates according to computer readable instructions to perform processing tasks. It should also be noted that in some implementations, a module may only be software, or only computer hardware, or only firmware. Although the present disclosure is described in terms of certain preferred embodiments, other embodiments will be apparent to those of ordinary skill in the art, given the benefit of this disclosure, including embodiments that do not provide all of the benefits and features set forth herein, which are also within the scope of this disclosure. It is to be understood that other embodiments may be utilized, without departing from the scope of the present disclosure.

What is claimed is:

1. A method of performing an implementation of a join operation, comprising:

receiving a join query comprising a join condition and an indication of a first relation and a second relation to be joined, wherein the join query is for an equality join operation;

separating the equality join operation into a build operation and a probe operation;

determining, by a processing device, an actual size of the second relation;

determining, by the processing device, to distribute at least one of the first and second relations using a broadcast join based at least in part on the actual size of the second relation;

in response to determining to distribute at least one of the first and second relations using the broadcast join, setting, by the processing device, a communication link between the first relation and at least one probe operator of the join query to a synchronous state; and duplicate the second relation to the at least one probe operator, the at least one probe operator to join the first relation and the second relation based on the join condition.

2. The method of claim 1, wherein determining to distribute at least one of the first and second relations using the broadcast join is further based on a cost metric associated with the broadcast join of the first relation and the second relation.

3. The method of claim 2, wherein the cost metric is a computational cost or a memory cost.

4. The method of claim 2, wherein determining to distribute at least one of the first and second relations using the broadcast join based on the cost metric comprises:

determining that the broadcast join is a most efficient type of join operation based on the cost metric.

5. The method of claim 1, further comprising distributing the second relation using the broadcast join, wherein using the broadcast join comprises assigning at least part of the second relation to two or more processing nodes associated with the first relation.

6. The method of claim 5, wherein distributing the second relation comprises duplicating the second relation across the two or more processing nodes associated with the first relation, and wherein during the duplication of the second relation the processing device forwards a local partition of the first relation to a local instance of a probe operator of the at least one probe operator for performing the join query.

7. The method of claim 6, wherein duplicating the second relation comprises broadcasting each partition of the second relation to every instance of the probe operator across the two or more processing nodes associated with the first relation.

8. The method of claim 1, wherein determining the actual size of the second relation is performed prior to performing the broadcast join.

9. The method of claim 1, wherein determining the actual size of the second relation comprises:
performing the build operation on the second relation to partition the second relation; and
determining, based on the build operation, the actual size of the second relation.

10. The method of claim 1, wherein the communication link in the synchronous state performs a local transfer of the first relation to a local instance of a probe operator of the at least one probe operator to perform the join query.

11. A system comprising:
a memory to store a plurality of relations; and
a processor, operatively coupled to the memory, the processor to:
receive a join query comprising a join condition and an indication of a first relation and a second relation to be joined, wherein the join query is for an equality join operation;
separate the equality join operation into a build operation and a probe operation;
determine an actual size of the second relation;
determine to distribute at least one of the first and second relations using a broadcast join based at least in part on the actual size of the second relation;
in response to determining to distribute at least one of the first and second relations using the broadcast join, set a communication link between the first relation and at least one probe operator of the join query to a synchronous state; and
duplicate the second relation to the at least one probe operator, the at least one probe operator to join the first relation and the second relation based on the join condition.

12. The system of claim 11, wherein to determine to distribute at least one of the first and second relations using the broadcast join is further based on a cost metric associated with the broadcast join of the first relation and the second relation.

13. The system of claim 12, wherein the cost metric is a computational cost or a memory cost.

14. The system of claim 12, wherein to determine to distribute at least one of the first and second relations using the broadcast join based on the cost metric, the processor is to:
determine that the broadcast join is a most efficient type of join operation based on the cost metric.

15. The system of claim 11, wherein the processor is further to distribute the second relation using the broadcast join, wherein to use the broadcast join the processor is to assign at least part of the second relation to two or more processing nodes associated with the first relation.

16. The system of claim 15, wherein to distribute the second relation the processor is to duplicate the second relation across the two or more processing nodes associated with the first relation, and wherein during the duplication of the second relation the processor is to forward a local partition of the first relation to a local instance of a probe operator of the at least one probe operator for performing the join query.

17. The system of claim 16, wherein to duplicate the second relation the processor is to broadcast each partition of the second relation to every instance of the probe operator across the two or more processing nodes associated with the first relation.

18. The system of claim 11, wherein the processor determines the actual size of the second relation prior to performing the broadcast join.

19. The system of claim 11, wherein to determine the actual size of the second relation the processor is to:
perform the build operation on the second relation to partition the second relation; and
determine, based on the build operation, the actual size of the second relation.

20. The system of claim 11, wherein the communication link in the synchronous state performs a local transfer of the first relation to a local instance of a probe operator of the at least one probe operator to perform the join query.

21. A non-transitory computer readable medium having instructions stored thereon that, when executed by a processor, cause the processor to:
receive a join query comprising a join condition and an indication of a first relation and a second relation to be joined, wherein the join query is for an equality join operation;
separate the equality join operation into a build operation and a probe operation;
determine, by the processor, an actual size of the second relation;
determine, by the processor, to distribute at least one of the first and second relations using a broadcast join based at least in part on the actual size of the second relation;
in response to determining to distribute at least one of the first and second relations using the broadcast join, set, by the processor, a communication link between the first relation and at least one probe operator of the join query to a synchronous state; and
duplicate the second relation to the at least one probe operator, the at least one probe operator to join the first relation and the second relation based on the join condition.

22. The non-transitory computer readable medium of claim 21, wherein to determine to distribute at least one of the first and second relations using the broadcast join is further based on a cost metric associated with the broadcast join of the first relation and the second relation.

23. The non-transitory computer readable medium of claim 22, wherein the cost metric is a computational cost or a memory cost.

24. The non-transitory computer readable medium of claim 22, wherein to determine to distribute at least one of the first and second relations using the broadcast join based on the cost metric the processor is to:
determine that the broadcast join is a most efficient type of join operation based on the cost metric.

25. The non-transitory computer readable medium of claim 21, wherein the processor is further to distribute the second relation using the broadcast join, wherein to use the broadcast join the processor is to assign at least part of the second relation to two or more processing nodes associated with the first relation.

26. The non-transitory computer readable medium of claim 25, wherein to distribute the second relation the processor is to duplicate the second relation across the two or more processing nodes associated with the first relation, and wherein during the duplication of the second relation the processor is to forward a local partition of the first relation to a local instance of a probe operator of the at least one probe operator for performing the join query.

27. The non-transitory computer readable medium of claim 26, wherein to duplicate the second relation the processor is to broadcast each partition of the second relation to every instance of the probe operator across the two or more processing nodes associated with the first relation.

28. The non-transitory computer readable medium of claim 21, wherein the processor determines the actual size of the second relation prior to performing the broadcast join.

29. The non-transitory computer readable medium of claim 21, wherein to determine the actual size of the second relation the processor is to:
  perform the build operation on the second relation to partition the second relation; and
  determine, based on the build operation, the actual size of the second relation.

30. The non-transitory computer readable medium of claim 21, wherein the communication link in the synchronous state performs a local transfer of the first relation to a local instance of a probe operator of the at least one probe operator to perform the join query.

\* \* \* \* \*

UNITED STATES PATENT AND TRADEMARK OFFICE
CERTIFICATE OF CORRECTION

PATENT NO. : 11,036,758 B2  
APPLICATION NO. : 17/085987  
DATED : June 15, 2021  
INVENTOR(S) : Dageville et al.

Page 1 of 1

It is certified that error appears in the above-identified patent and that said Letters Patent is hereby corrected as shown below:

In the Drawings

In Figure 3, please replace "MANAGEMEN T" with --MANAGEMENT--

In the Specification

In Column 5, Line 44, please replace "Baa" with --$\bowtie_\theta$--

In Column 5, Line 47, please replace "of must" with --of join must--

In Column 6, Line 18, please replace "|R|*n<|S|" with --|R|*n<|R|+|S|--

In Column 15, Line 36, please replace "link" with --link.--

Signed and Sealed this  
Twenty-third Day of May, 2023

Katherine Kelly Vidal  
*Director of the United States Patent and Trademark Office*